United States Patent
Dalal et al.

(10) Patent No.: US 7,927,284 B2
(45) Date of Patent: Apr. 19, 2011

(54) QUANTIFYING HEMODYNAMIC RESPONSE TO DRUG THERAPY USING IMPLANTABLE SENSOR

(75) Inventors: Yousufali H. Dalal, St. Louis Park, MN (US); Marina Brockway, Shoreview, MN (US); Richard O. Kuenzler, Shaker Heights, OH (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1352 days.

(21) Appl. No.: 11/431,806

(22) Filed: May 10, 2006

(65) Prior Publication Data
US 2007/0065363 A1    Mar. 22, 2007

Related U.S. Application Data

(60) Provisional application No. 60/717,961, filed on Sep. 16, 2005.

(51) Int. Cl.
*A61B 5/02* (2006.01)
(52) U.S. Cl. .......................... 600/504; 600/481; 600/483
(58) Field of Classification Search .................. 600/481, 600/483, 504
See application file for complete search history.

(56) References Cited

U.S. PATENT DOCUMENTS

| | | | |
|---|---|---|---|
| 4,562,841 A | 1/1986 | Brockway et al. | |
| 4,928,688 A | 5/1990 | Mower | |
| 5,036,849 A | 8/1991 | Hauck et al. | |
| 5,133,353 A | 7/1992 | Hauser | |
| 5,179,945 A | 1/1993 | VanHofwegen et al. | |
| 5,203,348 A | 4/1993 | Dahl et al. | |
| 5,230,337 A | 7/1993 | Dahl et al. | |
| 5,284,136 A | 2/1994 | Hauck et al. | |
| 5,313,953 A | 5/1994 | Yomtov et al. | |
| 5,314,459 A | 5/1994 | Swanson et al. | |
| 5,318,597 A | 6/1994 | Hauck et al. | |
| 5,334,222 A | 8/1994 | Salo et al. | |
| 5,360,442 A | 11/1994 | Dahl et al. | |
| 5,366,496 A | 11/1994 | Dahl et al. | |
| 5,376,106 A | 12/1994 | Stahmann et al. | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,540,727 A | 7/1996 | Tockman et al. | |

(Continued)

FOREIGN PATENT DOCUMENTS

WO    WO 97/18856    5/1997

OTHER PUBLICATIONS

U.S. Appl. No. 11/805,311, filed May 23, 2007, Thompson et al.

(Continued)

*Primary Examiner* — Charles A Marmor, II
*Assistant Examiner* — Karen E Toth
(74) *Attorney, Agent, or Firm* — Hollingsworth & Funk, LLC

(57) ABSTRACT

Systems and methods provide for assessing a patient's hemodynamic response to a drug therapy. A patient's hemodynamic response to a drug therapy is monitored using sensor data acquired using one or more sensors. The patient's hemodynamic response to the drug therapy is quantified, such as by quantifying a patient's sensitivity or refractoriness to the drug therapy. The quantified data may be used to optimize a patient's drug therapy, among other uses.

26 Claims, 7 Drawing Sheets

U.S. PATENT DOCUMENTS

| | | | |
|---|---|---|---|
| 5,545,202 A | 8/1996 | Dahl et al. | |
| 5,603,732 A | 2/1997 | Dahl et al. | |
| 5,620,466 A | 4/1997 | Haefner et al. | |
| 5,662,688 A | 9/1997 | Haefner et al. | |
| 5,682,901 A * | 11/1997 | Kamen | 600/519 |
| 5,836,987 A | 11/1998 | Baumann et al. | |
| 5,882,352 A | 3/1999 | Duncan et al. | |
| 5,916,243 A | 6/1999 | KenKnight et al. | |
| 6,026,320 A | 2/2000 | Carlson et al. | |
| 6,044,298 A | 3/2000 | Salo et al. | |
| 6,055,454 A | 4/2000 | Heemels | |
| 6,221,011 B1 | 4/2001 | Chen | |
| 6,270,457 B1 | 8/2001 | Bardy | |
| 6,277,072 B1 | 8/2001 | Bardy | |
| 6,280,380 B1 | 8/2001 | Bardy | |
| 6,285,907 B1 | 9/2001 | Kramer et al. | |
| 6,312,378 B1 | 11/2001 | Bardy | |
| 6,336,903 B1 | 1/2002 | Bardy | |
| 6,358,203 B2 | 3/2002 | Bardy | |
| 6,360,127 B1 | 3/2002 | Ding et al. | |
| 6,368,284 B1 | 4/2002 | Bardy | |
| 6,371,922 B1 | 4/2002 | Baumann et al. | |
| 6,398,728 B1 | 6/2002 | Bardy | |
| 6,411,848 B2 | 6/2002 | Kramer et al. | |
| 6,424,865 B1 | 7/2002 | Ding | |
| 6,440,066 B1 | 8/2002 | Bardy | |
| 6,459,929 B1 | 10/2002 | Hopper et al. | |
| 6,542,775 B2 | 4/2003 | Ding et al. | |
| 6,597,951 B2 | 7/2003 | Kramer et al. | |
| 6,666,826 B2 | 12/2003 | Salo et al. | |
| 6,892,095 B2 | 5/2005 | Salo | |
| 6,908,437 B2 | 6/2005 | Bardy | |
| 6,993,389 B2 | 1/2006 | Ding et al. | |
| 7,142,911 B2 | 11/2006 | Boileau | |
| 7,643,875 B2 * | 1/2010 | Heil et al. | 607/2 |
| 2002/0058877 A1 * | 5/2002 | Baumann et al. | 600/485 |
| 2003/0130702 A1 | 7/2003 | Kramer et al. | |
| 2003/0216792 A1 | 11/2003 | Levin et al. | |
| 2004/0077995 A1 * | 4/2004 | Ferek-Petric et al. | 604/66 |
| 2004/0167410 A1 * | 8/2004 | Hettrick | 600/486 |
| 2004/0225332 A1 * | 11/2004 | Gebhardt et al. | 607/17 |
| 2004/0230230 A1 | 11/2004 | Lindstrom et al. | |
| 2004/0230243 A1 | 11/2004 | Haefner et al. | |
| 2005/0137481 A1 | 6/2005 | Sheard | |
| 2005/0137626 A1 | 6/2005 | Pastore et al. | |
| 2006/0069322 A1 | 3/2006 | Zhang et al. | |
| 2006/0206267 A1 * | 9/2006 | Kirkland et al. | 701/220 |
| 2006/0258952 A1 | 11/2006 | Stahmann et al. | |
| 2008/0119750 A1 * | 5/2008 | Patangay et al. | 600/528 |

OTHER PUBLICATIONS

Boyle et al., "Redefining the Therapeutic Objective in Decompensated Heart Failure: Hemoconcentration as a Surrogate for Plasma Refill Rate", Journal of Cardiac Failure, vol. 12, No. 4, 2006.
Francis et al., Acute Vasoconstrictor Response to IV Furosemide in Patients with Chronic Congestive Heart Failure, Annals of Internal Medicine, vol. 130, No. 1, 1985.
International Search Report and Written Opinion dated Dec. 22, 2008 for PCT Application No. PCT/US2008/006526, 14 pages.
International Preliminary Report on Patentability dated Dec. 3, 2009 for PCT Application No. PCT/US2008/006526, 5 pages.
Office Action dated Apr. 27, 2010 for EP Application No. 08754635.4, 2 pages.
Office Action dated Apr. 29, 2010 for U.S. Appl. No. 11/805,311, 10 pages.
Office Action Response dated Jan. 25, 2010 for U.S. Appl. No. 11/805,311, 8 pages.
Office Action dated Dec. 24, 2009 for U.S. Appl. No. 11/805,311, 9 pages.

* cited by examiner

| Date | Curvature |
|---|---|
| 10/22/2004 | 1.332 |
| 10/25/2004 | 1.4177 |
| 11/22/2004 | 0.6667 |
| 11/25/2004 | 1.333 |
| 11/29/2004 | 0.3333 |
| 1/28/2005 | 0.9068 |
| 1/31/2005 | 0.344 |
| 2/14/2005 | 0.8045 |
| 3/21/2005 | 0.7214 |
| 3/28/2005 | 0.6143 |

QUANTIFYING HEMODYNAMIC RESPONSE TO DRUG THERAPY USING IMPLANTABLE SENSOR

RELATED APPLICATIONS

This application claims the benefit of Provisional Patent Application Ser. No. 60/717,961, filed on Sep. 16, 2005, to which priority is claimed pursuant to 35 U.S.C. §119(e) and which is hereby incorporated herein by reference.

FIELD OF THE INVENTION

The present invention relates generally to drug management and, more particularly, to quantifying a patient's hemodynamic response to a drug therapy using sensor data acquired via a medical device, such as an implantable medical device.

BACKGROUND OF THE INVENTION

Day-to-day management of patients with various diseases and disorders, such as chronic heart failure (HF), requires accurate clinical assessment of patient hemodynamics. The complex neurohormonal mechanisms that are activated by left ventricular (LV) dysfunction, for example, can lead to fluid volume overload and increase in LV filling pressure. This may be exacerbated by minor changes in salt and water intake, anemia, and changes in a drug regimen. The changes often cause cardiac decompensation and accumulation of fluid in lungs, leading to costly hospitalizations and progressive worsening of heart failure. Timely clinical intervention may prevent worsening of a patient's HF status, requiring accurate and timely assessment of patient state.

An HF patient typically takes a multitude of drugs to alleviate symptoms and control the disease progression. The therapy targets vary between drugs and patients. For example, drugs that lead to neurohormonal improvement (e.g., Beta-blockers, ACE-inhibitors) should be titrated to the target dosage. Diuretics, on the other hand, need to be optimized on a continuous basis to maintain hemodynamic balance.

SUMMARY OF THE INVENTION

The present invention is directed to systems and methods for assessing a patient's hemodynamic response to a drug therapy. Embodiments of the present invention are directed to quantifying a patient's hemodynamic response to a drug therapy. Assessing a patient's hemodynamic response to a drug therapy in accordance with the present invention provides for quantification of a patient's sensitivity to a drug therapy.

According to embodiments of the present invention, a drug therapy is delivered to a patient. Sensor data is acquired using an implantable medical device. A hemodynamic response of the patient to the drug therapy is quantified using the acquired sensor data. Quantifying the hemodynamic response of the patient may involve quantifying a sensitivity of the patient's hemodynamic response to the drug therapy, typically with knowledge of dosage and time of drug delivery. This knowledge may be derived automatically by monitoring the sensor arrangements as described herein. Quantifying the hemodynamic response of the patient may also involve indicating a degree of patient refractoriness to the drug therapy. Quantifying the hemodynamic response of the patient may be based on continuously acquired sensor data or sensor data acquired on a periodic or intermittent basis. Quantifying the hemodynamic response of the patient comprises may involve calculating a rate of change in acquired sensor data from pre- to post-drug therapy.

The quantified hemodynamic response of the patient to the drug therapy may be used for a variety of purposes, such as monitoring for drug therapy compliance of the patient. The patient's quantified hemodynamic response to the drug therapy may be used for adjusting the drug therapy delivered to the patient. The patient's quantified hemodynamic response may also be used for informing one or both of a clinician and the patient of the patient's hemodynamic status and/or alerting one or both of a clinician and the patient of a need for drug therapy adjustment. For example, parameters may be detected to quantify drug sensitivity of the patient, wherein one, some, or all of the parameters are trended for one or more of monitoring the drug therapy for compliance, refractoriness, titration, and optimization of the drug therapy, generating alerts to a clinician, physician, or the patient, and triggering automatic release of a drug from an implanted drug pump.

The implantable medical device may include a sensor arrangement configured to measure one or a number of hemodynamic parameters of the patient. The implantable medical device may, for example, include a sensor arrangement configured to measure one or more of a blood (internal filling) pressure, electrical activity of the patient's heart, impedance changes within the patient, heart sounds, blood chemicals, and other physiological parameters. In other configurations, the medical device may be a patient-external medical device that includes a sensor arrangement configured to externally measure one or a number of hemodynamic parameters of the patient, such as those identified above and elsewhere herein.

According to embodiments of the present invention, quantifying the hemodynamic response of the patient involves trending the acquired sensor data. Quantifying the hemodynamic response of the patient may involve, for example, generating a trending curve using the acquired sensor data, and fitting an $n^{th}$-order polynomial to the trending curve, where n is an integer greater than or equal to 1. Ensemble averaging of the fitting curve may be performed to cumulatively monitor the change in drug sensitivity over days, weeks, or months of drug therapy. A highest order coefficient of the $n^{th}$-order polynomial may be used to indicate an extent of trending curve flattening, wherein trending curve flattening is indicative of reduced sensitivity of the patient's hemodynamic response to the drug therapy. Quantifying can also include comparing the trending curve to trending curves previously generated during high patient sensitivity to a drug of the drug therapy or during initiation or calibration associated with sensor data acquisition. Quantifying can further include calculating the rate of change of the acquired sensor data pre- and post-drug therapy.

In various embodiments, quantifying the hemodynamic response of the patient may be performed within the implantable medical device. In other embodiments, quantifying the hemodynamic response of the patient is performed using a patient-external system.

According to further embodiments of the present invention, systems for monitoring a patient's hemodynamic response to a drug therapy include an implantable medical device comprising a sensor arrangement configured to acquire sensor data. A processor is coupled to the sensor arrangement. The processor is configured to quantify a hemodynamic response of the patient to the drug therapy using the acquired sensor data. The processor may be disposed within the implantable medical device or within a patient-external system, such as a programmer, personal communicator or networked patient management server, for example.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
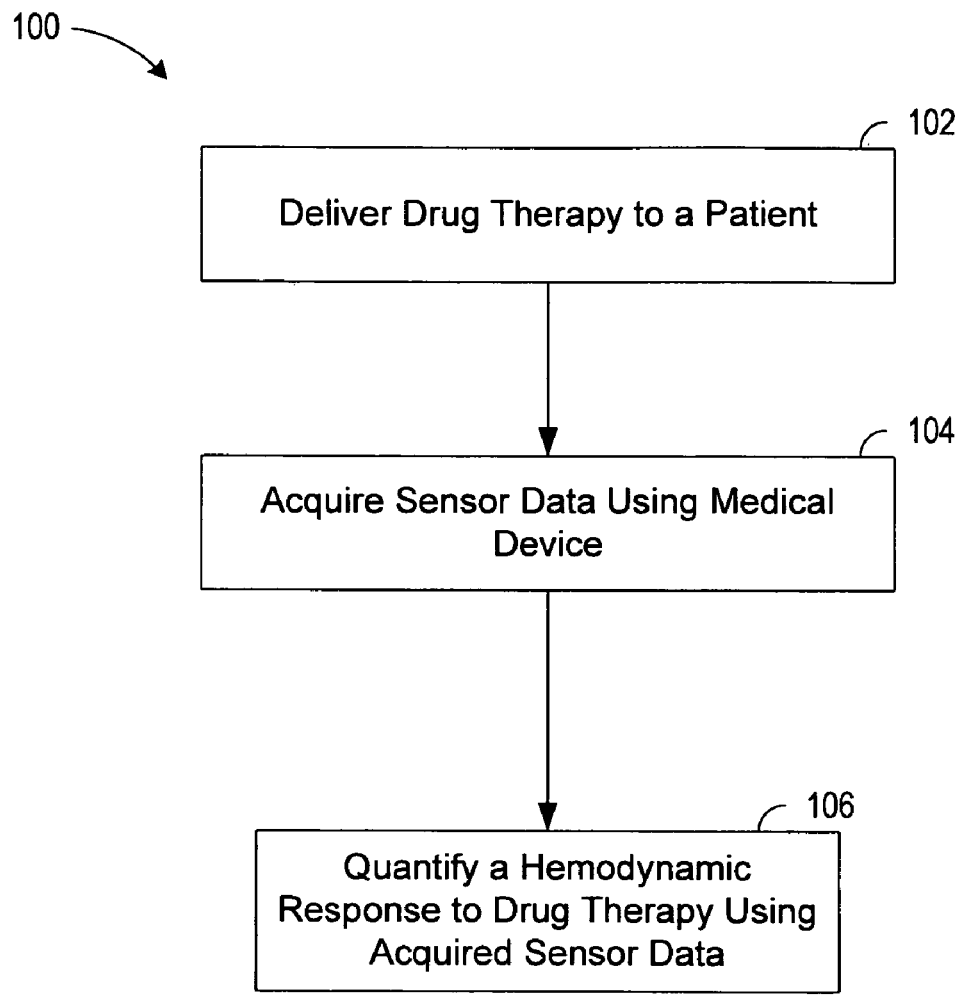
FIG. 1 is a flow diagram of a method for assessing a patient's hemodynamic response to a drug therapy in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

A medical device according to the present invention may include one or more of the features, structures, methods, or combinations thereof described hereinbelow. For example, a cardiac monitor, cardiac stimulator, or other type of implantable or patient-external medical device may be implemented to include one or more of the advantageous features and/or processes described below. It is intended that such a monitor, stimulator, or other external, implanted or partially implanted device need not include all of the features described herein, but may be implemented to include selected features that provide for useful structures and/or functionality. Such a device may be implemented to provide a variety of therapeutic or diagnostic functions.

A wide variety of implantable medical devices, such as cardiac sensing and/or stimulation devices, may be configured to implement a hemodynamic response quantification methodology of the present invention. A non-limiting, representative list of such devices includes cardiac monitors, pacemakers, cardiovertors, defibrillators, resynchronizers, and other cardiac sensing and therapy delivery devices. These devices may be configured with a variety of electrode arrangements, including surface, transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

A variety of devices other than cardiac monitoring/stimulation devices may also be implemented to provide for hemodynamic response quantification, such as external and implantable drug delivery devices equipped with an external or implantable hemodynamic sensor or nerve stimulation devices equipped with an implantable or external hemodynamic sensor, for example. Such devices are referred to herein generally as a patient-implantable medical device (PIMD) for convenience, it being understood that such a medical device may alternatively be implemented as a patient-external medical device.

The present invention is directed to systems and methods for assessing a patient's hemodynamic response to a drug therapy. Embodiments of the present invention are directed to quantifying a patient's hemodynamic response to a drug therapy. Assessing a patient's hemodynamic response to a drug therapy in accordance with the present invention provides for quantification of a patient's sensitivity to a drug therapy, such as by indicating when and to what extent a patient becomes refractory to a particular drug. Managing a patient's drug regimen in accordance with the present invention provides for quantification of individual patient response to a drug, such as a diuretic, in the presence of other drugs, different dosages, posture changes, and other patient conditions that can change over time.

Providing a clinician or physician with a quantified response of the patient to a given drug therapy permits the clinician or physician to better understand the patient's individual drug response and facilitates optimization of the patient's drug regimen. In the absence of quantified response data made available by embodiments of the present invention, the clinician or physician is limited to traditional techniques of adjusting drug dosages and/or frequency of delivery based on judgment and/or professional norms.

Problems arising from such traditional approaches to drug therapy management are of particular concern for patients that suffer from heart failure, for example. Maintaining hemodynamic balance in patients suffering from HF is critical to improved quality of life and prevention of decompensation episodes that cause such patients to frequently return to the hospital. For example, it is estimated that nearly one million hospital admissions for acute decompensated heart failure (HF) occur in the United States each year, which is almost double the number admitted 15 years ago. The rehospitalization rates during the 6 months following discharge are as much at 50%. Nearly 2% of all hospital admissions in the United States are for decompensated HF patients, and heart failure is the most frequent cause of hospitalization in patients older than 65 years. The average duration of hospitalization is about 6 days. Despite aggressive therapies, hospital admissions for HF continue to increase, reflecting the prevalence of this malady.

Presently, physicians attempt to maintain hemodynamic balance in HF patients by titrating a slew of symptom reducing drugs, such as diuretics, and neurohormonal drugs, such as Beta-blockers. This is done during times of follow-ups, severe symptomatic distress, and/or hospitalizations. Minimal day-to-day chronic management is done to optimize such medications. Furthermore, since no quantification of patient response to drug regimens is performed, these drugs are titrated using qualitative observations and assessment, such as by doubling dosages or increasing drug administration frequency, for example. Consequently, since a patient's physiologic state changes with the pathophysiology of the HF disease, the patient response to the drug varies with successive interventions.

Providing physicians with a quantified response of the patient to a drug therapy overcomes problems associated with conventional drug titration approaches by providing objective data from which physicians may gain access to an individual patient's physiologic state, and allows for the delivery of optimal drug therapy to the patient.

Turning now to FIG. 1, there is illustrated a method 100 of assessing a patient's hemodynamic response to a drug therapy in accordance with embodiments of the present invention. According to the method 100 shown in FIG. 1, a drug therapy is delivered to, or taken by, a patient 102. Sensor data is acquired 104 using a medical device, which is preferably an implantable device but may alternatively be a patient-external device. A hemodynamic response to the drug therapy is quantified 106 using the acquired sensor data 106.

By way of example, data acquired by an implantable sensor may be trended after delivery of a particular drug, such as a diuretic, to a patient afflicted with edema. Upon successive treatment for edema with the diuretic, the sensor data curve may appear to flatten out, which indicates that the same dosing of the drug is not providing the same beneficial effect as it did in previous interventions. The trended data provides quantified evidence to the physician that the patient is becoming progressively more refractory to the drug. The physician may appropriately adjust the drug therapy delivered to the patient, and the patient's hemodynamic response to the adjusted therapy may again be assessed and quantified to arrive at an optimal drug regimen for the patient.

Figure 2:
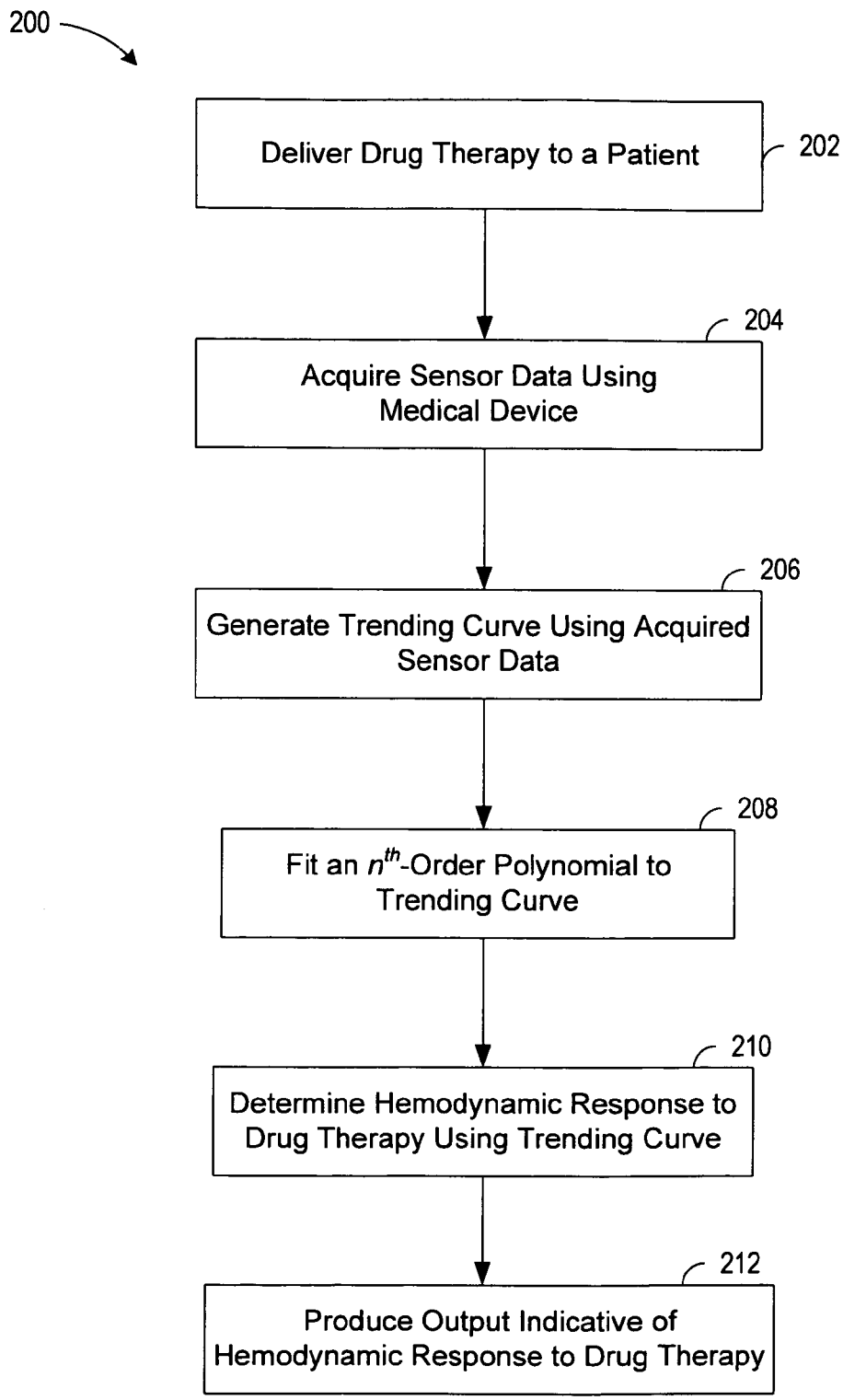
FIG. 2 is a flow diagram of a method for assessing a patient's hemodynamic response to a drug therapy in accordance with other embodiments of the present invention.

FIG. 2 illustrates a method 200 of assessing a patient's hemodynamic response to a drug therapy in accordance with other embodiments of the present invention. According to the method 200, a drug therapy is delivered 202 to a patient. Sensor data is acquired 204 using a medical device, preferably an implantable medical device but may alternatively be a patient-external device. A trending curve is generated 206 using the acquired sensor data. An $n^{th}$-order polynomial curve is fitted 208 to the trending curve. It is understood that other curve fitting techniques may be employed. A hemodynamic response to the drug therapy is determined 210 using the trending curve. An output indicative of the patient's hemodynamic response to the drug therapy is produced 212.

In one embodiment, and as discussed previously, a $2^{nd}$-order polynomial may be fitted to the trending curve. Ensemble averaging of the fitting curve may be performed to cumulatively monitor the change in drug sensitivity over days, weeks, or months of drug therapy. The highest order coefficient (e.g., curvature) indicates the extent of curve flattening. The closer the highest order coefficient is to zero, the flatter the response. Flattening of the trending curve provides quantified evidence that the patient is becoming or has become refractory to the administered drug. Current and past trending curves may be compared to reveal useful information concerning the patient's response to a drug therapy and for purposes of sensor initialization and calibration. For example, a trending curve can be compared to a trending curve previously generated during high patient sensitivity to a drug of the drug therapy or during initiation or calibration associated with sensor data acquisition. Trending curves provide a useful visual tool that allows physicians or clinician to assess the sensitivity or insensitivity of the patient to a drug regimen.

Figure 3:
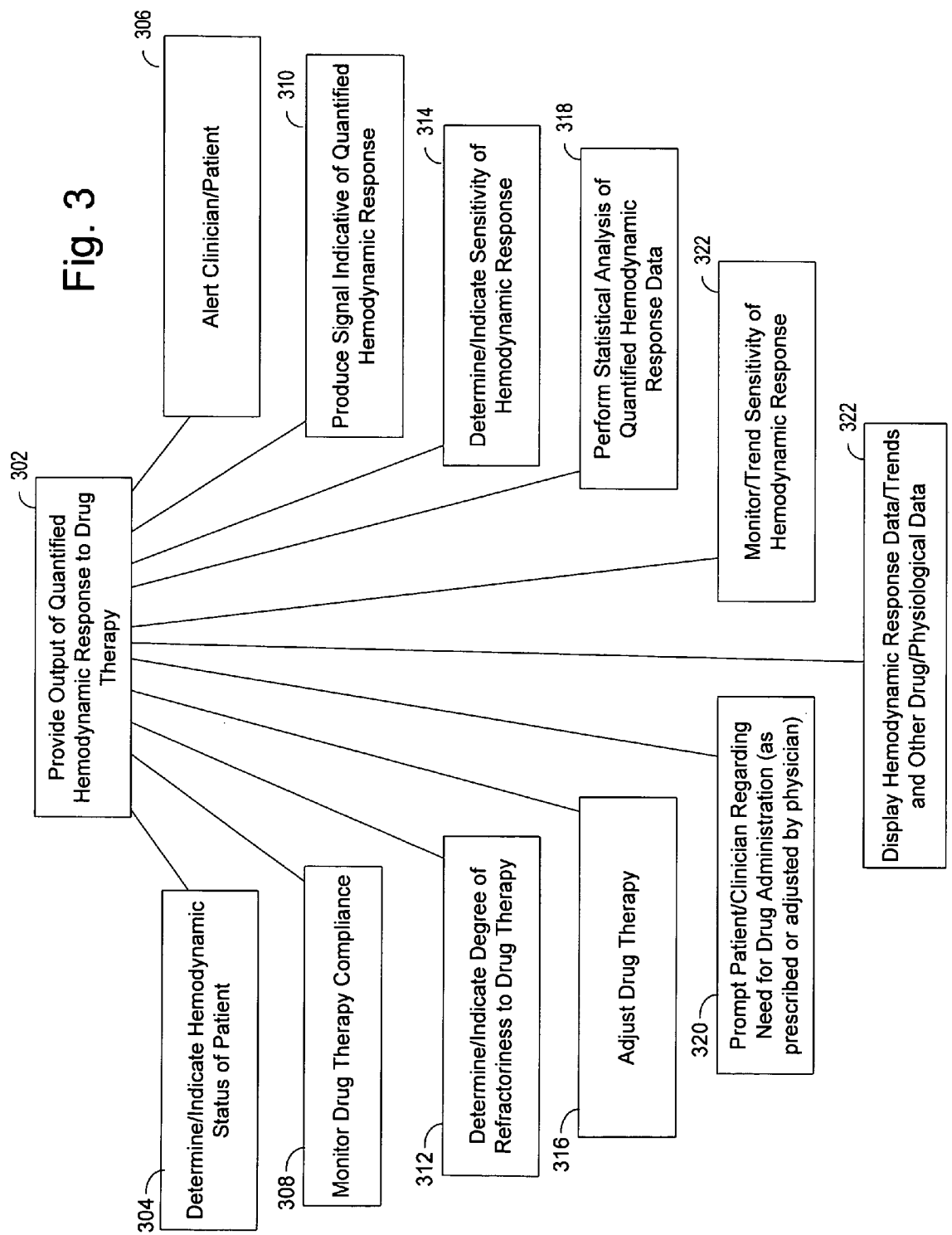
FIG. 3 is a block diagram showing a variety of illustrative operations that may be performed in response to an output indicative of a patient's quantified hemodynamic response to a drug therapy in accordance with embodiments of the present invention.

FIG. 3 is a block diagram showing a variety of illustrative operations that may be performed in response to an output indicative of a patient's quantified hemodynamic response to a drug therapy in accordance with embodiments of the present invention. As is shown in FIG. 3, an output of a patient's quantified hemodynamic response to a drug therapy is provided 302. This output may take various forms and be used for a variety of purposes. The output may be produced by a medical device implanted within the patient. The output may also be produced by a patient-external device that receives sensor data from a medical device implanted within the patient. Other output scenarios are contemplated.

As is shown in FIG. 3, the hemodynamic status of the patient may be determined or indicated 304 using the output 302. An alert to the clinician and/or patient 306 may be generated and communicated in various forms to the clinician and/or patient in response to the output 302. Drug therapy compliance by the patient may be monitored 308 using the output 302. A signal indicative of the patient's quantitative hemodynamic response may be produced 310 and take several forms, including an electrical or electromagnetic signal, optical signal, or acoustic signal, for example.

A degree of patient refractoriness to the drug therapy may be determined or indicated 312 based on the output 302. A sensitivity of the patient's hemodynamic response to the drug therapy may be determined or indicated 314. The drug therapy may be adjusted or titrated 316 as discussed above. Statistical analyses of hemodynamic response data may be initiated or performed 318 in response to the output 302.

The patient and/or clinician may be prompted 320, such as by audible, textual, or visual means, as to the need for drug administration as originally prescribed or adjusted by the physician. A patient's sensitivity of hemodynamic response to the drug regimen may be monitored and/or trended 322, such as in the manner discussed above. A variety of hemodynamic response data, trend data, and other drug and physiological data may be displayed 322 for use by the patient, clinician, and/or physician. FIG. 3 is intended to provide a non-exhaustive, non-limiting listing of examples concerning the use of quantified hemodynamic response data acquired using an implantable or patient-external medical device in accordance with the principles of the present invention.

Figure 4:
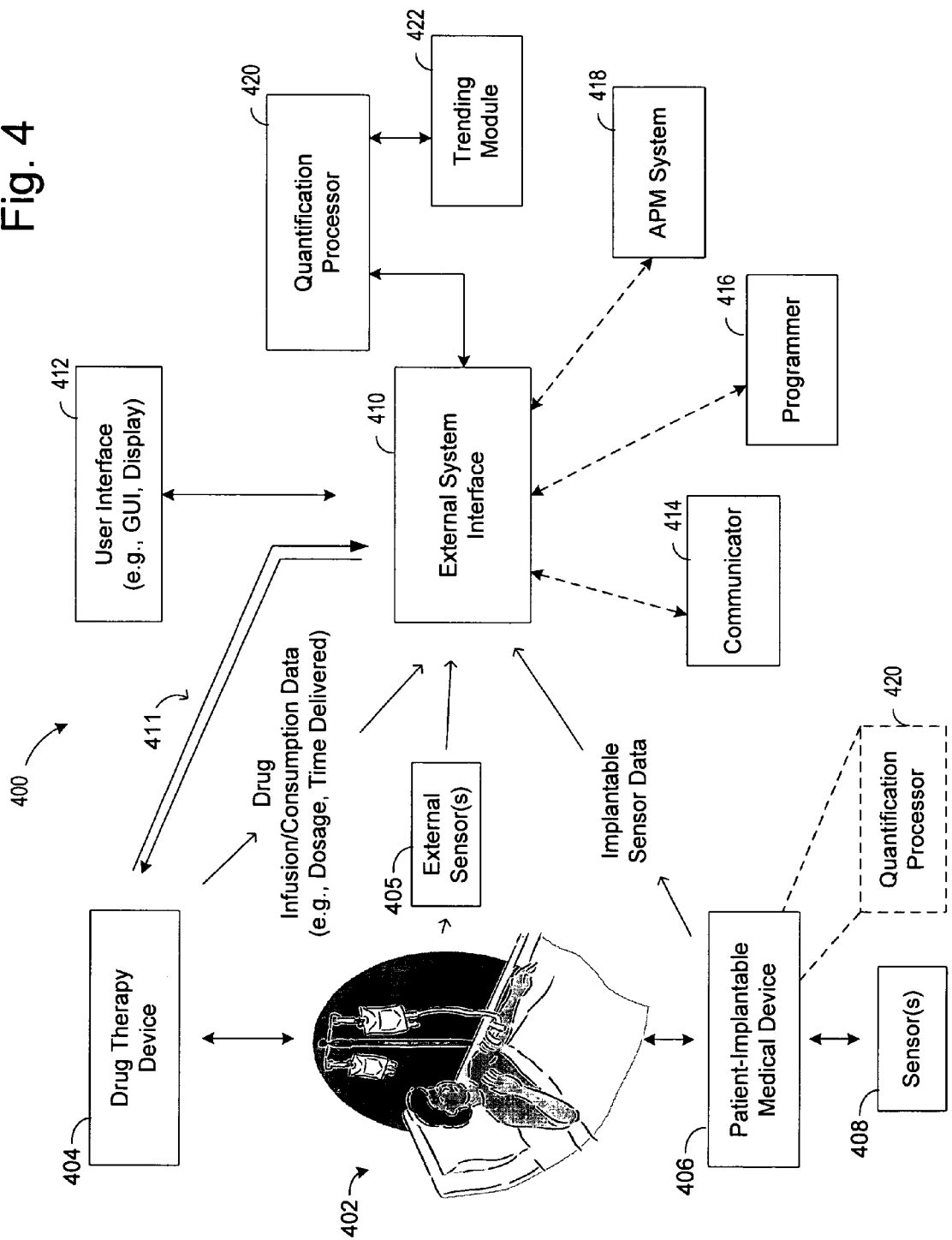
FIG. 4 is a block diagram of a system for managing patient drug delivery based on a quantified hemodynamic response of the patient to the drug delivery in accordance with embodiments of the present invention.

FIG. 4 is a block diagram of a system 400 for managing patient drug delivery based on a quantified hemodynamic response of the patient to the drug delivery in accordance with embodiments of the present invention. FIG. 4 shows a patient 402 that is receiving drug therapy as prescribed by a physician. The drug therapy may be delivered to the patient 402 by infusion using a drug therapy device 404, such as a drug pump device. The drug therapy may also be delivered by patient consumption of the prescribed medication, in which case the drug therapy device 404 may represent a pill counting device or drug consumption questionnaire, for example.

The system 400 shown in FIG. 4 includes a patient-implantable medical device 406 that is implanted in the patient 402. PIMD 402 incorporates or is coupled to one or more implantable sensors 408. One or more of the sensors 408 are configured to sense a hemodynamic parameter or condition of the patient. Such sensors 408 may include one or more of a blood (internal filling) pressure sensor, blood flow sensor, blood temperature sensor, heart sounds sensor (e.g., accelerometer or microphone), impedance sensor (e.g., implanted transthoracic total impedance sensor) and blood chemistry or composition sensor (e.g., $PO_2$ sensor, $SAO_2$ sensor, glucose sensor, lactate sensor, $PCO_2$ sensor, pH sensor, and molecular probe). Examples of suitable blood (internal filling) pressure sensors, blood flow sensors, blood temperature sensors, and associated detection techniques are described in commonly-owned U.S. Pat. Nos. 6,666,826 and 6,892,095, which are hereby incorporated herein by reference.

A variety of external sensors 405 may also be used to sense various physiological parameters of the patient. Such external sensors 405 may include one or more of a pulse oximetry sensor, blood pressure sensor, blood chemistry sensor, patient temperature sensor, EKG sensor arrangement, among others.

The system 400 includes a number of patient-external devices. An external system interface 410 includes communication circuitry configured to effect communications with PIMD 406. External system interface 410 may also be configured to effect communications with the drug therapy device 404, such as by a unidirectional or bi-directional communication link. External system interface 410 may further be configured to effect communications with external sensors 405.

Uni-directional communications facilitates the transfer of drug therapy information (e.g., drug type, dosage, day/time of administration) from the drug therapy device 404 to the external system interface 410. It is understood that the external system interface 410 may be integral to, or separate from, the drug therapy device 404 in various embodiments. Bi-directional communications facilitates closed-loop management of the patient's drug therapy, which preferably allows for physician input/intervention within the loop established between the drug therapy device 404 and PIMD 406. This system configuration advantageously allows for automatic or semi-automatic titration of a drug therapy delivered to a patient.

The external system interface 410 may be communicatively coupled to, or integral with, one or more of a programmer 416, an advanced patient management system 418, a portable or hand-held communicator 414, or other patient-external system. The external system interface 410 is coupled to a user interface 412, such as a graphical user interface or other interface that provides a display. User interface 412 preferably includes a user actuatable input/output device, such as a keyboard, touch screen sensor, mouse, light pen, and the like. The user interface 412 may be used to input drug therapy information, such as type of drug(s) being administered, dosage of such drugs, times and dates of drug administration, patient information, including patient weight, perception of wellness, and other information relevant to the patient's condition or drug regimen.

A quantification processor 420 is shown coupled to the external system interface 410. Alternatively, quantification processor 420 may be incorporated as a component of the PIMD 406, as is shown in phantom. The quantification processor 420 may also be incorporated as a component of the communicator 414, programmer 416, or APM system 418.

The quantification processor 420 performs the various processes described above and provides quantified hemodynamic response data to the external system interface 410 for display to the physician, clinician, and/or patient via the user interface 412, for example.

Figures 5, 6:
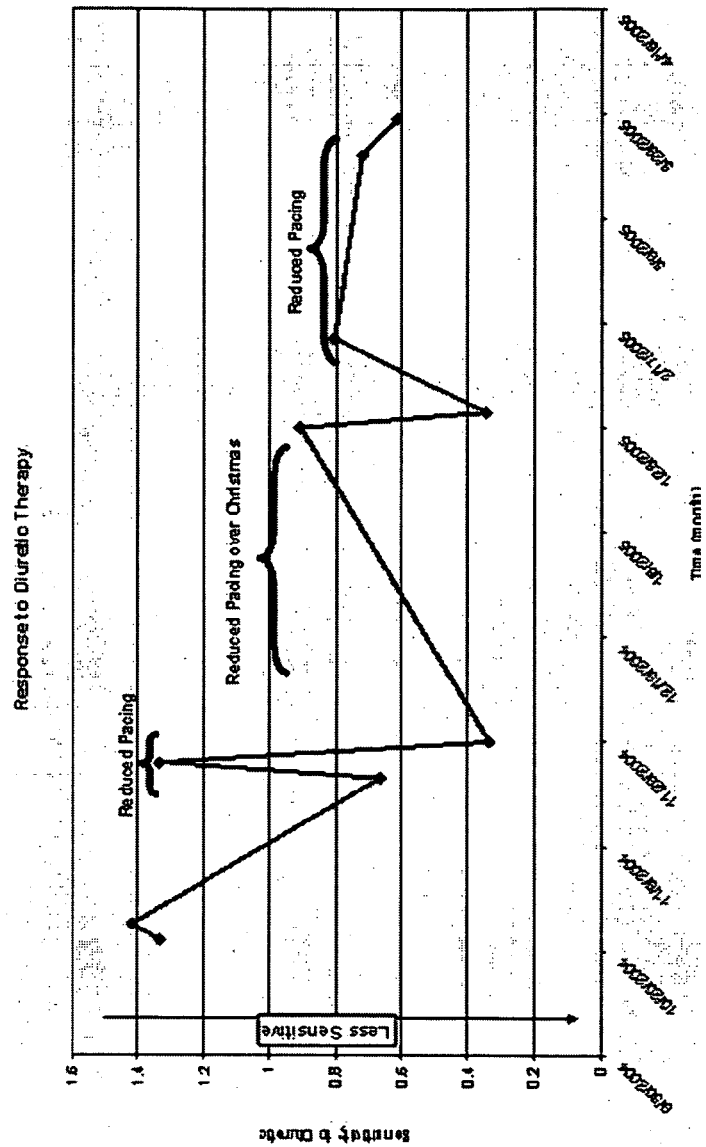
FIG. 5 is a table that quantifies curvature (and hence sensitivity to the drug) from a second-order polynomial fit to hemodynamic sensor data acquired from an implantable sensor in accordance with embodiments of the present invention.
FIG. 6 is a graphical representation of the data tabulated in FIG. 5.

Turning now to FIG. 5, there is shown a table that quantifies curvature (and hence sensitivity to the drug) from a second-order polynomial fit to hemodynamic sensor data acquired from an implantable sensor in accordance with embodiments of the present invention. FIG. 6 is a graphical representation of the data tabulated in FIG. 5. FIGS. 5 and 6 demonstrate the ability to measure the acute response to a drug, such as a diuretic, and indicate to the physician changes, chronologically, in drug-sensitivity due to the status (e.g., HF status) of the patient. A worsening in HF status of the patient causes the curvature of the trending curve in FIG. 6 to get closer to zero and hence the response time of the therapy is longer (or not existent).

The data of FIGS. 5 and 6 demonstrate that the effect of the drug is reliably detectable by the implantable sensor. FIGS. 5 and 6 further demonstrate that drug effect may be monitored and used to provide effective therapy to HF patients or other patient disease states. Using one or more implantable sensors, such as those described above, a patient's hemodynamic response to a diuretic, for example, may be monitored, quantified, and relayed to the physician to optimally treat patients with different doses or types of diuretics. Issues of compliance, refractoriness to medication, and optimization may also be targeted. For example, present clinical practice optimizes diuretic regimen by adding thiazide diuretics to loop diuretics to increase fluid reduction. A drug therapy management approach consistent with the principles of the present invention can target and improve such clinical practice.

Various embodiments described herein may be used in connection with devices that provide for HF monitoring, diagnosis, and/or therapy. A patient implantable medical device or PIMD of the present invention may incorporate HF features involving dual-chamber or bi-ventricular pacing/therapy, cardiac resynchronization therapy, cardiac function optimization, or other HF related methodologies. For example, a PIMD of the present invention may incorporate features of one or more of the following references: commonly owned U.S. Pat. Nos. 6,411,848; 6,285,907; 4,928,688; 6,459,929; 5,334,222; 6,026,320; 6,371,922; 6,597,951; 6,424,865; 6,542,775; and 7,260,432, each of which is hereby incorporated herein by reference.

Certain configurations illustrated herein are generally described as capable of implementing various functions traditionally performed by an implantable cardioverter/defibrillator (ICD), and may operate in numerous cardioversion/defibrillation modes as are known in the art. Examples of ICD circuitry, structures and functionality, aspects of which may be incorporated in a PIMD of the present invention, are disclosed in commonly owned U.S. Pat. Nos. 5,133,353; 5,179,945; 5,314,459; 5,318,597; 5,620,466; and 5,662,688, which are hereby incorporated herein by reference.

In particular configurations, systems and methods may perform functions traditionally performed by pacemakers, such as providing various pacing therapies as are known in the art, in addition to cardioversion/defibrillation therapies. Examples of pacemaker circuitry, structures and functionality, aspects of which may be incorporated in a PIMD of the present invention, are disclosed in commonly owned U.S. Pat. Nos. 4,562,841; 5,284,136; 5,376,106; 5,036,849; 5,540,727; 5,836,987; 6,044,298; and 6,055,454, which are hereby incorporated herein by reference. It is understood that PIMD configurations may provide for non-physiologic pacing support in addition to, or to the exclusion of, bradycardia and/or anti-tachycardia pacing therapies.

A PIMD in accordance with the present invention may implement diagnostic and/or monitoring functions as well as provide cardiac stimulation therapy. Examples of cardiac monitoring circuitry, structures and functionality, aspects of which may be incorporated in a PIMD of the present invention, are disclosed in commonly owned U.S. Pat. Nos. 5,313,953; 5,388,578; and 5,411,031, which are hereby incorporated herein by reference.

Figure 7:
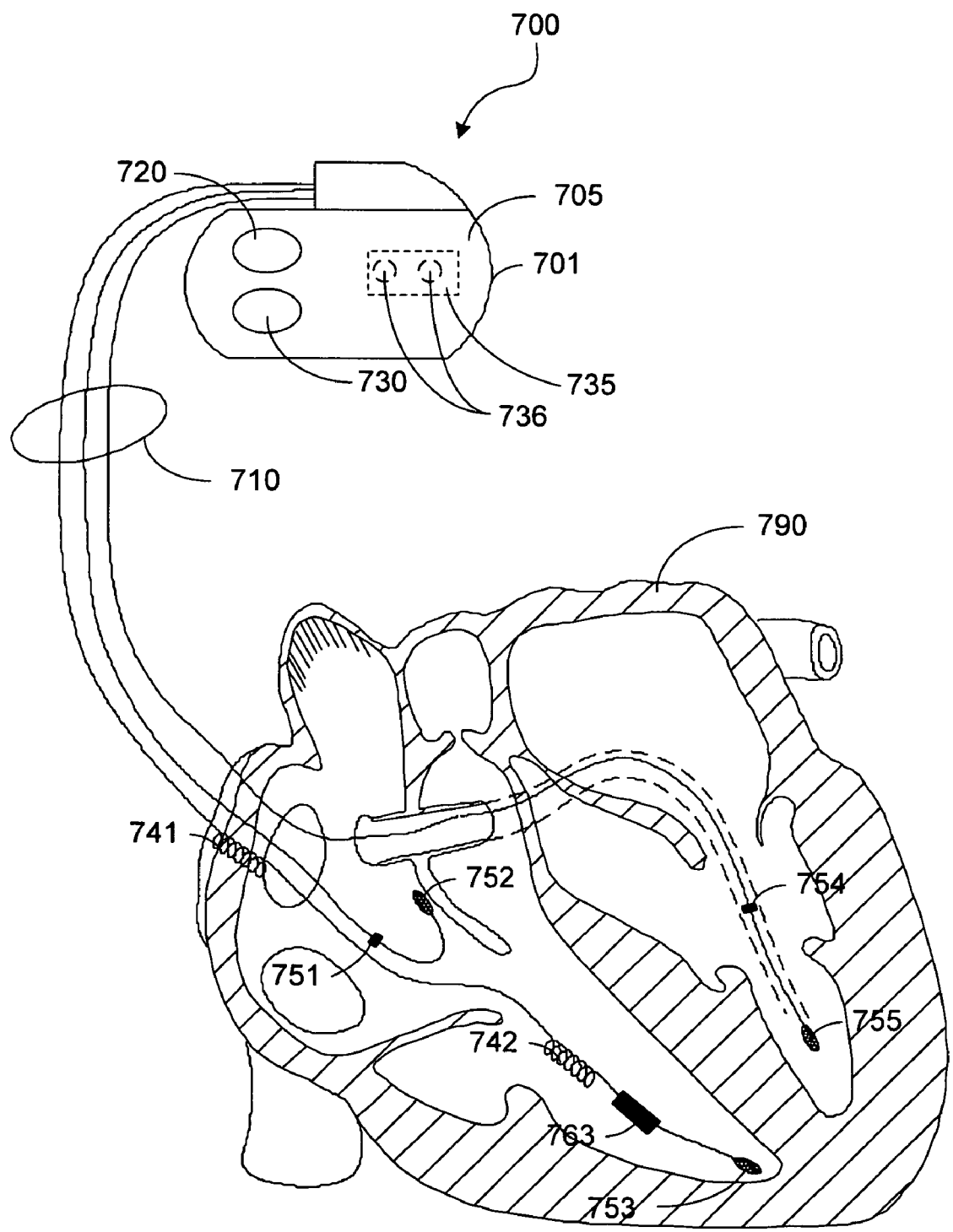
FIG. 7 is an illustration of an implantable cardiac device including a lead assembly shown implanted in a sectional view of a heart, the implantable cardiac device implemented to sense one or more hemodynamic parameters of a patient in accordance with embodiments of the invention.

Referring now to FIG. 7, there is illustrated an embodiment of a PIMD configured to sense one or more hemodynamic parameters for purposes of quantifying a hemodynamic response to a patient's drug therapy in accordance with embodiments of the present invention. In this illustrative example, the PIMD includes a cardiac rhythm management device (CRM) 700 including an implantable pulse generator 705 electrically and physically coupled to an intracardiac lead system 710.

Portions of the intracardiac lead system 710 are inserted into the patient's heart 790. The intracardiac lead system 710 includes one or more electrodes and/or sensors configured to sense electrical cardiac activity of the heart, deliver electrical stimulation to the heart, sense the patient's transthoracic impedance or transthoracic total impedance, sense blood (internal filling) pressure, blood flow, and/or blood temperature, sense acceleration and/or body acoustics, and/or sense other physiological parameters. Portions of the housing 701 of the pulse generator 705 may optionally serve as a can electrode.

Communications circuitry is disposed within the housing 701 for facilitating communication between the pulse generator 705 and an external communication device, such as a portable or bed-side communication station, patient-carried/worn communication station (e.g., communicator), external programmer or advanced patient management system interface, for example. The communications circuitry may also facilitate unidirectional or bidirectional communication with one or more implanted, external, cutaneous, or subcutaneous physiologic or non-physiologic sensors, patient-input devices and/or information systems.

The pulse generator 705 may optionally incorporate a motion detector 720 that may be used to sense patient activity as well as various respiration and cardiac related conditions. For example, the motion detector 720 may be optionally configured to sense snoring, activity level, and/or chest wall movements associated with respiratory effort, for example. The motion detector 720 may be implemented as an accelerometer positioned in or on the housing 701 of the pulse generator 705. For a motion sensor implemented as an accelerometer, the motion sensor may also provide respiratory, e.g. rales, coughing, and cardiac, e.g. S1-S4 heart sounds, murmurs, and other acoustic information. An accelerometer may be used to develop respiration waveforms from which various respiratory parameters may be developed.

The lead system 710 and pulse generator 705 of the CRM 700 may incorporate one or more transthoracic impedance sensors that may be used to acquire the patient's respiration waveform, or other respiration-related information. The transthoracic impedance sensor may include, for example, one or more intracardiac electrodes 741, 742, 751-755, 763 positioned in one or more chambers of the heart 790. The intracardiac electrodes 741, 742, 751-755, 763 may be coupled to impedance drive/sense circuitry 730 positioned within the housing of the pulse generator 705.

In one implementation, impedance drive/sense circuitry 730 generates a current that flows through the tissue between an impedance drive electrode 751 and a can electrode on the housing 701 of the pulse generator 705. The voltage at an impedance sense electrode 752 relative to the can electrode changes as the patient's transthoracic impedance changes. The voltage signal developed between the impedance sense electrode 752 and the can electrode is detected by the impedance sense circuitry 730. Other locations and/or combinations of impedance sense and drive electrodes are also possible.

The lead system 710 may include one or more cardiac pace/sense electrodes 751-755 positioned in, on, or about one or more heart chambers for sensing electrical signals from the patient's heart 790 and/or delivering pacing pulses to the heart 790. The intracardiac sense/pace electrodes 751-755, such as those illustrated in FIG. 7, may be used to sense and/or pace one or more chambers of the heart, including the left ventricle, the right ventricle, the left atrium and/or the right atrium. The lead system 710 may include one or more defibrillation electrodes 741, 742 for delivering defibrillation/cardioversion shocks to the heart.

The lead system 710 may include one or more leads each having one or more electrodes that extend into the heart. FIG. 7 shows three such leads, one that extends into the right atrium, one that extends into the right ventricle, and one that extends into a coronary vein for placement at the surface of the left ventricle. The left ventricular lead, in particular, includes an LV distal electrode 755 and an LV proximal electrode 754 located at appropriate locations in or about the left ventricle for pacing and/or sensing the left ventricle. The left ventricular lead may be guided into the right atrium of the heart via the superior vena cava. From the right atrium, the left ventricular lead may be deployed into the coronary sinus ostium, the opening of the coronary sinus. The lead may be guided through the coronary sinus to a coronary vein of the left ventricle. This vein is used as an access pathway for leads to reach the surfaces of the left ventricle that are not directly accessible from the right side of the heart.

The pulse generator 705 may include circuitry for detecting cardiac arrhythmias and/or for controlling pacing or defibrillation therapy in the form of electrical stimulation pulses or shocks delivered to the heart through the lead system 710. The pulse generator 705 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and 6,993,389, which are hereby incorporated herein by reference.

For purposes of illustration, and not of limitation, various embodiments of devices implemented in accordance with the present invention are described herein in the context of PIMDs that may be implanted under the skin in the chest region of a patient. A PIMD may, for example, be implanted subcutaneously such that all or selected elements of the device are positioned on the patient's front, back, side, or other body locations suitable for sensing cardiac activity and/or delivering cardiac stimulation therapy. It is understood that elements of the PIMD may be located at several different body locations, such as in the chest, abdominal, or subclavian region with electrode elements respectively positioned at different regions near, around, in, or on the heart.

The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature.

In a further implementation, for example, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present invention are described in commonly owned, co-pending U.S. Publication No. 2004/0230230 and U.S. Pat. No. 7,499,750, which are hereby incorporated herein by reference.

Figure 8:
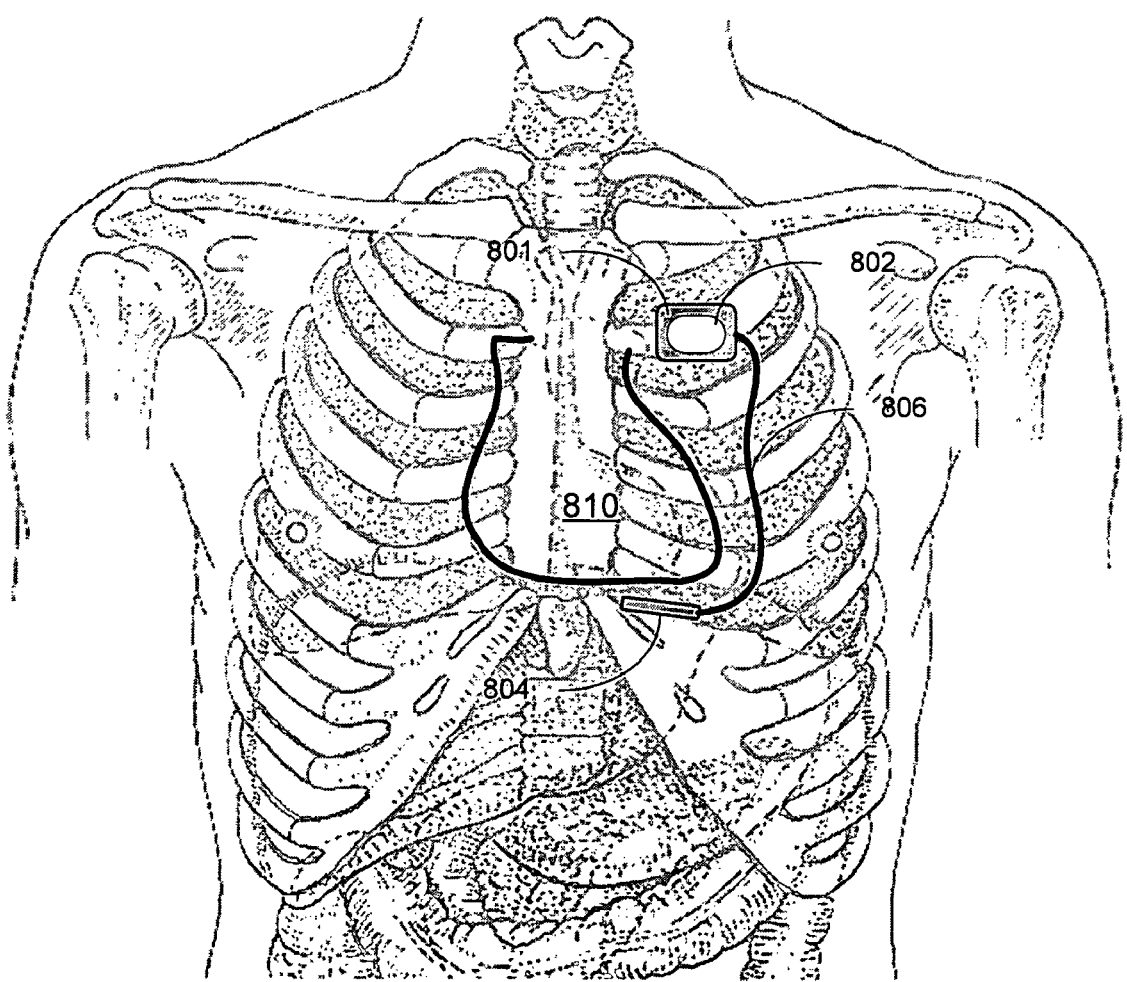
FIG. 8 is an illustration of an implantable medical device including a subcutaneous, non-intrathoracic lead assembly shown implanted outside the ribcage, the implantable medical device implemented to sense one or more hemodynamic parameters of a patient in accordance with embodiments of the invention.

In one configuration, as is illustrated in FIG. 8, electrode subsystems of a PIMD system are arranged about a patient's heart 810. The PIMD system includes a first electrode subsystem, comprising a can electrode 802, and a second electrode subsystem 804 that includes at least two electrodes or at least one multi-element electrode. The second electrode subsystem 804 may include a number of electrodes used for sensing and/or electrical stimulation.

In various configurations, the second electrode subsystem 804 may include a combination of electrodes. The combination of electrodes of the second electrode subsystem 804 may include coil electrodes, tip electrodes, ring electrodes, multi-element coils, spiral coils, spiral coils mounted on non-conductive backing, screen patch electrodes, and other electrode configurations as will be described below. A suitable non-conductive backing material is silicone rubber, for example.

The can electrode 802 is positioned on the housing 801 that encloses the PIMD electronics. In one embodiment, the can electrode 802 includes the entirety of the external surface of housing 801. In other embodiments, various portions of the housing 801 may be electrically isolated from the can electrode 802 or from tissue. For example, the active area of the can electrode 802 may include all or a portion of either the anterior or posterior surface of the housing 801 to direct current flow in a manner advantageous for cardiac sensing and/or stimulation. For example, portions of the housing 801 may be covered with a non-conductive, or otherwise electrically resistive, material to direct current flow. Suitable non-conductive material coatings include those formed from silicone rubber, polyurethane, or parylene, for example.

The PIMD system shown in FIG. 8 incorporates one or more sensors configured to sense a parameter useful for assessing hemodynamic status. A sensor may be disposed on housing 801, such that element 802 may be representative of such sensor(s) alone or in combination with a can electrode. A sensor(s) may be disposed on another component of the PIMD system, such as on lead 806, a lead separate from lead 806, or on the subsystem element 804, which may be representative of such sensor(s) alone or in combination with a cardiac electrode.

A PIMD of the present invention may be implemented to communicate with a patient management server or network via an appropriate communications interface or an external programmer. A PIMD of the present invention may be used within the structure of an advanced patient management (APM) system. The advanced patient management system allows physicians to remotely and automatically monitor cardiac and respiratory functions, as well as other patient conditions. In one example, a PIMD implemented as a cardiac pacemaker, defibrillator, or resynchronization device may be equipped with various telecommunications and information technologies that enable real-time data collection, diagnosis, and treatment of the patient. Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

The components, functionality, and structural configurations depicted herein are intended to provide an understanding of various features and combination of features that may be incorporated in a PIMD or patient-external medical device. It is understood that a wide variety of PIMDs, external medical devices, and other implantable cardiac monitoring and/or stimulation device configurations are contemplated, ranging from relatively sophisticated to relatively simple designs. As such, particular medical device configurations may include particular features as described herein, while other such device configurations may exclude particular features described herein.

Various modifications and additions can be made to the preferred embodiments discussed hereinabove without departing from the scope of the present invention. For example, the methods and systems described herein generally include an implantable device or sensor for measuring one or more hemodynamic parameters of the patient. It is understood that methods and systems of the present invention may be implemented using patient-external devices and sensors, and that the embodiments described herein may be implemented in the context of such patient-external devices and sensors. Accordingly, the scope of the present invention should not be limited by the particular embodiments described above, but should be defined only by the claims set forth below and equivalents thereof.

What is claimed is:

1. A system for monitoring drug therapy sensitivity with information concerning administration of a drug therapy to a patient and the patient's hemodynamic response to the drug therapy, the system comprising:
    an implantable sensor arrangement configured to acquire sensor data indicative of the patient's hemodynamic response to the drug therapy; and
    a processor configured to receive the sensor data and the information concerning administration of the drug therapy to the patient, the processor further configured to generate a trending curve based on the sensor data and the information concerning administration of the drug therapy and quantify a sensitivity of the hemodynamic response of the patient to the drug therapy using the trending curve, the processor configured to determine the information concerning delivery of the drug therapy to the patient based on the sensor data.

2. The system of claim 1, wherein the processor is disposed within an implantable medical device.

3. The system of claim 1, wherein the processor is disposed within a patient-external system.

4. The system of claim 1, wherein the processor is configured to quantify the sensitivity of the patient's hemodynamic response to the drug therapy based on flattening of the trending curve, wherein trending curve flattening is indicative of reduced sensitivity of the patient's hemodynamic response to the drug therapy.

5. The system of claim 1, wherein the processor is configured to fit an $n^{th}$-order polynomial to the trending curve as part of quantifying the sensitivity of the hemodynamic response of the patient to the drug therapy, wherein n is an integer greater than or equal to 1.

6. The system of claim 5, wherein the processor is configured to use a highest order coefficient of the $n^{th}$-order polynomial to indicate an extent of trending curve flattening to quantify the sensitivity of the hemodynamic response.

7. The system of claim 5, wherein the processor is configured to ensemble average the $n^{th}$-order polynomial to cumulatively monitor change in drug sensitivity over a period of time.

8. The system of claim 1, wherein the processor is configured to compare the trending curve to a trending curve previously generated during high patient sensitivity to a drug of the drug therapy or during initiation or calibration associated with sensor data acquisition.

9. The system of claim 1, wherein the processor is configured to determine a degree of patient refractoriness to the drug therapy based on the trending curve.

10. The system of claim 1, wherein the information concerning administration of the drug therapy to the patient comprises dosage and time of delivery of a drug to the patient.

11. The system of claim 1, further comprising an implantable drug delivery device configured to deliver the drug therapy.

12. The system of claim 11, wherein the sensor arrangement is coupled to the implantable drug delivery device.

13. The system of claim 11, wherein the implantable drug delivery device is a drug pump device.

14. The system of claim 11, wherein the processor is configured to adjust delivery of the drug therapy by the implantable drug delivery device based on the quantification of the sensitivity of the hemodynamic response of the patient.

15. The system of claim 1, wherein the processor is configured to identify a change in heart failure status of the patient based on the quantification of the sensitivity of the hemodynamic response of the patient.

16. The system of claim 1, wherein the trending curve represents days, weeks, or months of hemodynamic response data.

17. The system of claim 1, further comprising a user interface device in communication with the processor, wherein the processor is further configured to cause the user interface device to display an indication of the quantification of the sensitivity of the hemodynamic response of the patient to the drug therapy.

18. The system of claim 1, wherein the processor is configured to adjust the drug therapy delivered to the patient based on the quantification of the sensitivity of the hemodynamic response of the patient to the drug therapy.

19. The system of claim 1, wherein the processor is configured to generate an alert indicating a need for drug therapy adjustment based on the quantification of the hemodynamic response of the patient to the drug therapy.

20. The system of claim 1, wherein the implantable sensor arrangement is configured to sense internal filling blood pressure.

21. The system of claim 1, wherein the implantable sensor arrangement is configured to sense blood flow.

22. The system of claim 1, wherein the implantable sensor arrangement is configured to sense blood temperature.

23. The system of claim 1, wherein the implantable sensor arrangement is configured to measure one or more blood chemicals.

24. The system of claim 1, wherein the implantable sensor arrangement is configured to measure heart sounds.

25. The system of claim 1, wherein the drug therapy comprises administration of a diuretic.

26. A system for monitoring drug therapy sensitivity with information concerning administration of a drug therapy to a patient and the patient's hemodynamic response to the drug therapy, the system comprising:

an implantable sensor arrangement configured to acquire sensor data indicative of the patient's hemodynamic response to the drug therapy; and a processor configured to receive the sensor data and the information concerning administration of the drug therapy to the patient, the processor further configured to generate a trending curve based on the sensor data and the information concerning administration of the drug therapy and quantify a sensitivity of the hemodynamic response of the patient to the drug therapy using the trending curve, the processor configured to monitor drug therapy compliance of the patient using the quantification of the sensitivity of the hemodynamic response of the patient to the drug therapy.

* * * * *